(12) United States Patent  
Lim et al.

(10) Patent No.: US 6,682,759 B2
(45) Date of Patent: Jan. 27, 2004

(54) MANUFACTURE OF ORAL DOSAGE FORMS DELIVERING BOTH IMMEDIATE-RELEASE AND SUSTAINED-RELEASE DRUGS

(75) Inventors: Jong C. Lim, San Jose, CA (US); John N. Shell, Rocklin, CA (US)

(73) Assignee: DepoMed, Inc., Menlo Park, CA (US)

( * ) Notice: Subject to any disclaimer, the term of this patent is extended or adjusted under 35 U.S.C. 154(b) by 35 days.

(21) Appl. No.: 10/066,146

(22) Filed: Feb. 1, 2002

(65) Prior Publication Data

US 2003/0147952 A1 Aug. 7, 2003

(51) Int. Cl.$^7$ .............. A61K 9/22; A61K 9/24; A61K 9/26; A61K 9/36
(52) U.S. Cl. .......... 424/468; 424/469; 424/470; 424/472; 424/474; 424/479; 424/480; 424/486; 424/488
(58) Field of Search ............... 424/468, 469, 424/470, 472, 474, 479, 480, 482, 486, 488, 484

(56) References Cited

U.S. PATENT DOCUMENTS

| | | |
|---|---|---|
| 4,024,175 A | 5/1977 | Satzinger et al. |
| 4,292,299 A | 9/1981 | Suzuki et al. |
| 4,786,503 A | 11/1988 | Edgren et al. |
| 4,894,476 A | 1/1990 | Butler et al. |
| 5,085,865 A | 2/1992 | Nayak |
| 5,162,117 A | 11/1992 | Stupak et al. |
| 5,549,913 A | 8/1996 | Colombo et al. |
| 5,681,583 A | 10/1997 | Conte et al. |
| 5,780,057 A | 7/1998 | Conte et al. |
| 5,837,379 A | 11/1998 | Chen et al. |
| 5,861,173 A | 1/1999 | Nishioka et al. |
| 5,922,769 A | 7/1999 | Barelli et al. |
| 5,972,389 A | 10/1999 | Shell et al. |
| 6,011,049 A | 1/2000 | Whitcomb |
| 6,054,482 A | 4/2000 | Augart et al. |
| 6,056,977 A | 5/2000 | Bhagwat et al. |
| 6,099,862 A | 8/2000 | Chen et al. |
| 6,126,969 A | 10/2000 | Shah et al. |
| 6,153,632 A | 11/2000 | Rieveley |
| 6,171,618 B1 * | 1/2001 | Johnson et al. ............. 424/472 |
| 6,183,777 B1 | 2/2001 | Chen et al. |
| 6,183,778 B1 | 2/2001 | Conte et al. |
| 6,194,000 B1 * | 2/2001 | Smith et al. ................ 424/458 |
| 6,211,205 B1 | 4/2001 | Ikeda et al. |
| 6,270,797 B1 | 8/2001 | Gidwani et al. |
| 6,294,690 B1 | 9/2001 | Deering et al. |
| 6,372,255 B1 | 4/2002 | Saslawski et al. |
| 2001/0018070 A1 | 8/2001 | Shell et al. |
| 2001/0036478 A1 | 11/2001 | Adjei et al. |

FOREIGN PATENT DOCUMENTS

| | | |
|---|---|---|
| EP | 0795324 A2 | 9/1997 |
| EP | 0598309 B1 | 1/1998 |
| GB | 1 330 829 | 9/1973 |
| WO | WO 00/23045 | 4/2000 |

OTHER PUBLICATIONS

Baichwal, A. and Neville, D.A. "Culturing Innovation and Enhancing Medications Using Oral Drug Delivery," *Drug Delivery Technology* May 2002, pp. 65–68, vol. 2, No. 3.
Halsas et al., *S.T.P. Pharma Sciences* 8:3: 155–161 (1998).
Sirkia et al., *S.T.P. Pharma Sciences* 3:6 453–458 (1993).
Sirkia et al., *International Journal of Pharmaceuticals* 107: 179–187 (1994).
Sirkia et al., *European Journal of Pharmaceutical Sciences* 1: 195–201 (1994).
Lee, "Controlled release of dual drug–loaded hydroxypropyl methylcellulose matrix tablet using drug–containing polymeric coatings" *International Journal of Pharmaceutics* 188, pp. 71–80, (1999).

* cited by examiner

*Primary Examiner*—James M. Spear
(74) *Attorney, Agent, or Firm*—M. Henry Heines; Townsend and Townsend and Crew LLP

(57) ABSTRACT

A method is disclosed for manufacturing a pharmaceutical tablet for oral administration, the tablet combining both immediate-release and prolonged-release modes of drug delivery and using an immediate-release drug that is either insoluble in water or only sparingly soluble and is present in a very small amount compared to the prolonged-release drug. The method involves the use of particles of the immediate-release drug that are equal to or less than 10 microns in diameter, applied as a layer or coating over a core of the prolonged-release drug, the layer or coating being either the drug particles themselves, applied as an aqueous suspension, or a solid mixture containing the drug in admixture with a material that disintegrates rapidly in gastric fluid. The result in both cases is a high degree of uniformity in the proportions of the immediate-release and prolonged-release drugs, uniformity that is otherwise difficult to achieve in view of the insolubility of the immediate-release drug and its relatively small amount compared to the prolonged-released drug.

14 Claims, No Drawings

MANUFACTURE OF ORAL DOSAGE FORMS DELIVERING BOTH IMMEDIATE-RELEASE AND SUSTAINED-RELEASE DRUGS

BACKGROUND OF THE INVENTION

1. Field of the Invention

This invention is in the field of pharmacology, and relates to drug dosage forms that are designed to deliver the drugs to human patients at particular rates.

2. Description of the Prior Art

Certain pharmacological therapies either require or benefit from the administration of drugs in a sequential manner. This can be done by a regimen in which the patient follows a prescribed time schedule, but because of patient noncompliance, scrupulous adherence to a schedule often requires the assistance of a medical professional. Even those therapies that involve only two dosages, such as an immediate but rapidly declining high-level dosage combined with a prolonged low-level or moderate-level dosage, either of the same drug or of two different drugs, can be a nuisance to the individual or troublesome to maintain if the individual is required to take separate unitary dosage forms. Certain pharmaceutical formulations have therefore been developed that combine both functions into a single dosage form. This simplifies the therapy and reduces or eliminates the chances of improper administration.

Many unitary dosage forms that have been proposed for combining immediate release with prolonged release do so by the placement of the drugs in different layers of a tablet or by placing one drug in a quickly-dissolving or quickly-dispersing coating over the surface of a slowly dissolving or swellable core that contains the other drug. With its high initial release concentration and rapid rate of decline, the immediate-release drug is often provided in a much lower amount than the prolonged-release drug. The immediate-release portion of the dosage form is therefore either a very thin layer or coating or a layer or coating with a very low concentration of the drug relative to the drug in the prolonged-released portion. It is common, for example, to design the dosage form such that the amount of drug intended for immediate release is 1/100th or less of the amount intended for prolonged release.

This large imbalance in the amounts of immediate-release and controlled-release drug creates problems in manufacturing, particularly in achieving uniformity from one tablet to the next. It is difficult to achieve uniform immediate-release coatings or layers of uniform drug content when the drug is so low in quantity or concentration. The problem is exacerbated when the drug in the immediate-release portion is one that has little or no solubility in water.

SUMMARY OF THE INVENTION

It has now been discovered that a dosage form that includes a core from which drug is released on a prolonged basis and a coating or layer from which drug is released on an immediate-release basis can be made in a manner that provides a high degree of uniformity in the immediate-release portion, even when the drug in the immediate-release portion is either insoluble or only sparingly soluble in water. This is achieved by limiting the drug particle diameter in the immediate-release coating or layer to 10 microns or less. The coating or layer is either the particles themselves, applied as an aqueous suspension, or a solid composition that contains the drug particles incorporated in a solid material that disintegrates rapidly in gastric fluid. Either mixture can be applied as a coating or layer over a core or coherent mass of the prolonged-release drug. When an aqueous suspension is used and applied as a coating, a suspending agent, binder, or both can be included to improve the procedure, and in either case, other excipients can be included to facilitate the manufacturing process.

Details on these and other features, advantages, and embodiments of the invention will be apparent from the description that follows.

DETAILED DESCRIPTION OF THE INVENTION AND PREFERRED EMBODIMENTS

The dosage forms of this invention are designed for oral ingestion, and the prolonged-release portion of the dosage form is one that delivers its drug to the digestive system continuously over a period of time of at least an hour and preferably several hours. The drug is retained in a matrix or supporting body of pharmaceutically inert solid, and the controlled delivery rate can be achieved by using a matrix that allows the gastric fluid to permeate the matrix and leach out the drug (i.e., allow the drug to diffuse out from the matrix as the drug slowly dissolves in the permeating fluid), or a matrix that slowly dissolves or erodes to expose the drug to the gastric fluid, or one that does both of these at once. The delivery rate is preferably slow enough that at least about 40% of the drug remains unreleased one hour after ingestion, more preferably at least about 60% and most preferably at least about 80%. In general, the drug will be substantially all released within about ten hours and preferably within about eight hours, and in most cases, the matrix supporting the drug will remain substantially intact until all of the drug is released. "Substantially intact" in this sense means that the matrix retains its size and shape without dissolving or disintegrating into fragments.

The immediate-release portion of the dosage form is either a coating applied or deposited over the entire surface of a unitary prolonged-release core, or a single layer of a tablet constructed in two or more layers, one of the other layers of which is the prolonged-released portion. Immediate release of the drug from the immediate-release layer is achieved by any of various methods known in the art. One example is the use of a very thin layer or coating which by virtue of its thinness is quickly penetrated by gastric fluid allowing fast leaching of the drug. Another example is by incorporating the drug in a mixture that includes a supporting binder or other inert material that dissolves readily in gastric fluid, releasing the drug as the material dissolves. A third is the use of a supporting binder or other inert material that rapidly disintegrates upon contact with gastric fluid, with both the material and the drug quickly dispersing into the fluid as small particles. Examples of materials that rapidly disintegrate and disperse are lactose and microcrystalline cellulose. An example of a suspending agent and binder is hydroxypropyl methyl cellulose.

The dosage forms of this invention include those in which the same drug is used in both the immediate-release and the prolonged-release portions as well as those in which one drug is formulated for immediate release and another drug, different from the first, for prolonged release. This invention is particularly directed to dosage forms in which the immediate-release drug is at-most sparingly soluble in water, i.e., either sparingly soluble or insoluble in water, while the prolonged-release drug can be of any level of solubility. The immediate-release drug is of sufficiently low solubility that it remains a solid particle during the preparation of the dosage form when the dosage form is prepared without the use of organic solvents. The only dispersing medium, when one is used, is water or an aqueous solution that may contain other components. The term "at most sparingly soluble" as used herein denotes a drug having a solubility in water at 37° C. that is generally less than 2% by weight, preferably less than 0.5% by weight. The particle size of the drug as it is used in the practice of this invention is equal to or less than about 10 microns in diameter, preferably within the range of from about 0.3 micron to about 10 microns in diameter, and most preferably with the range of from about 1 micron to about 5 microns in diameter.

The immediate-release drug can thus be deposited as a suspension over a unitary core of the controlled-release drug, with deposition being achieved by coating techniques known in the pharmaceutical formulation art such as spraying, pan coating, and the like, or the drug can be combined with particles of a binding matrix and compressed over a preformed layer of the controlled-release drug to form a layered tablet. In either case, the immediate-release coating or layer separates relatively quickly from the remainder of the tablet after ingestion, leaving the remainder intact. The weight ratio of the immediate-release drug to the prolonged-release drug is about 0.01:1 or less, preferably from about 0.001:1 to about 0.01:1.

In certain preferred embodiments of the invention, the supporting matrix in controlled-release portion of the tablet is a material that swells upon contact with gastric fluid to a size that is large enough to promote retention in the stomach while the subject is in the digestive state, which is also referred to as the postprandial or "fed" mode. This is one of two modes of activity of the stomach that differ by their distinctive patterns of gastroduodenal motor activity. The "fed" mode is induced by food ingestion and begins with a rapid and profound change in the motor pattern of the upper gastrointestinal (GI) tract. The change consists of a reduction in the amplitude of the contractions that the stomach undergoes and a reduction in the pyloric opening to a partially closed state. The result is a sieving process that allows liquids and small particles to pass through the partially open pylorus while indigestible particles that are larger than the pylorus are retropelled and retained in the stomach. This process causes the stomach to retain particles that are greater than about 1 cm in size for about 4 to 6 hours. The controlled-release matrix in these embodiments of the invention is therefore selected as one that swells to a size large enough to be retropelled and thereby retained in the stomach, causing the prolonged release of the drug to occur in the stomach rather than in the intestines.

Disclosures of oral dosage forms that swell to sizes that will prolong the residence time in the stomach are found in U.S. Pat. No. 5,007,790 ("Sustained-Release Oral Drug Dosage Form;" Shell, inventor; Apr. 16, 1991), U.S. Pat. No. 5,582,837 ("Alkyl-Substituted Cellulose-Based Sustained-Release Oral Drug Dosage Forms;" Shell, inventor; Dec. 10, 1996): U.S. Pat. No. 5,972,389 ("Gastric-Retentive Oral Drug Dosage Forms for the Controlled Release of Sparingly Soluble Drugs and Insoluble Matter;" Shell et al., inventors; Oct. 26, 1999); International (PCT) Patent Application WO 98/55107 ("Gastric-Retentive Oral Drug Dosage Forms for Controlled Release of Highly Soluble Drugs;" Shell et al., inventors; publication date Dec. 10, 1998); United States Patent Application Publication No. US 2001/0018707 A1 ("Extending the Duration of Drug Release Within the Stomach During the Fed Mode;" Shell et al., inventors, publication date Aug. 30, 2001); and International (PCT) Patent Application WO 96/26718 ("Controlled Release Tablet;" Kim, inventor: publication date Sep. 6, 1996). Each of the documents cited in this paragraph is incorporated herein in its entirety.

In general, swellable matrices contain binders that are water-swellable polymers, and suitable polymers are those that are non-toxic, that swell in a dimensionally unrestricted manner upon imbibition of water, and that release the drug gradually over time. Examples of polymers meeting this description are:

cellulose polymers and their derivatives including, but not limited to, hydroxymethyl cellulose, hydroxyethyl cellulose, hydroxypropyl cellulose, hydroxypropylmethyl cellulose, carboxymethylcellulose, and microcrystalline cellulose polysaccharides and their derivatives polyalkylene oxides polyethylene glycols chitosan poly(vinyl alcohol)

xanthan gum maleic anhydride copolymers poly(vinyl pyrrolidone)

starch and starch-based polymers maltodextrins poly (2-ethyl-2-oxazoline)

poly(ethyleneimine)

polyurethane hydrogels crosslinked polyacrylic acids and their derivatives

Further examples are copolymers of the polymers listed above, including block copolymers and graft polymers. Specific examples of copolymers are PLURONIC® and TECTONIC®, which are polyethylene oxide-polypropylene oxide block copolymers available from BASF Corporation, Chemicals Div., Wyandotte, Mich., USA. Further examples are hydrolyzed starch polyacrylonitrile graft copolymers, commonly known as "Super Slurper" and available from Illinois Corn Growers Association, Bloomington, Ill., USA.

Particularly preferred polymers are poly(ethylene oxide), hydroxypropyl methyl cellulose, and combinations of poly (ethylene oxide) and hydroxypropyl methyl cellulose.

As indicated above, the dosage forms of the present invention find utility when administered to subjects who are either in the fed mode or the fasting mode. Administration during the fed mode is preferred, since the narrowing of the pyloric opening that occurs in the fed mode serves as a further means of promoting gastric retention by retaining a broader range of smaller dosage form sizes.

The fed mode is normally induced by food ingestion, but can also be induced pharmacologically by the administration of pharmacological agents that have an effect in this regard that is the same or similar to that of a meal. These fed-mode inducing agents may be administered separately or they may be included in the dosage form as an ingredient dispersed in the dosage form or in an outer immediate-release coating. Examples of pharmacological fed-mode inducing agents are disclosed in co-pending U.S. patent application Ser. No. 09/432,881, filed Nov. 2, 1999, entitled "Pharmacological Inducement of the Fed Mode for Enhanced Drug Administration to the Stomach," inventors Markey, Shell, and Berner, the contents of which are incorporated herein by reference.

The size, shape, and dimensions of the tablet are not critical to the invention, provided that in embodiments where a swellable matrix is used, the tablet is sufficiently sized that upon swelling it reaches the dimensions that will be retained in the stomach during the fed mode. The tablet may be circular or elongated. An elongated tablet may be 18 to 22 mm in length, 6.5 to 10 mm in width, and 6.2 to 7.5 mm in height. A specific example is one that is 20 mm in length, 6.7 mm in width, and 6.4 mm in height. Again, these are merely examples; the shapes and sizes can be varied considerably.

Tablets in accordance with this invention can be prepared by conventional mixing, comminution, and tabletting techniques that are well known in the pharmaceutical formulations industry. The controlled-release portion can for example be fabricated by direct compression by punches and dies fitted to a rotary tabletting press, ejection or compression molding, granulation followed by compression, or forming a paste and extruding the paste into a mold or cutting the extrudate into short lengths. The immediate-release portion can be applied as a coating over the controlled-release portion by spraying, dipping, or pan-coating, or as an additional layer by tabletting or compression in the same manner as the controlled-release portion.

When tablets are made by direct compression, the addition of lubricants may be helpful and is sometimes important to promote powder flow and to prevent capping of the tablet (the breaking off of a portion of the tablet) when the pressure is relieved. Useful lubricants are magnesium stearate (in a concentration of from 0.25% to 3% by weight, preferably about 1% or less by weight, in the powder mix), and hydrogenated vegetable oil (preferably hydrogenated and refined triglycerides of stearic and palmitic acids at about 1% to 5% by weight, most preferably about 2% by weight). Additional excipients may be added to enhance powder flowability, tablet hardness, and tablet friability and to reduce adherence to the die wall.

The drug that is contained in the controlled release portion of the tablet may be any chemical compound, complex or composition that is suitable for oral administration and that has a beneficial biological effect, preferably a therapeutic effect in the treatment of a disease or an abnormal physiological condition. The drug can be either a high-solubility drug or a sparingly soluble or insoluble drug, all referring to solubility in water or aqueous media. Examples of high solubility drugs are metformin hydrochloride, vancomycin hydrochloride, captopril, lisinopril, erythromycin lactobionate, ranitidine hydrochloride, sertraline hydrochloride, ticlopidine hydrochloride, baclofen, amoxicillin, cefuroxime axetil, cefaclor, clindamycin, levodopa, doxifluridine, tramadol, fluoxitine hydrochloride, bupropion, potassium chloride, and esters of ampicillin. Examples low solubility drugs are saguinavir, ritonavir, nelfinavir, thiamphenicol, ciprofloxacin, calcium carbonate, clarithromycin, azithromycin, ceftazidime, acyclovir, ganciclovir, cyclosporin, digoxin, paclitaxel, iron salts, topiramate, ketoconazole, and sulfonylureas such as glimepiride, glypuride, and glipizide. Other drugs suitable for use will be apparent to those skilled in the art. This invention is of particular interest for antibiotics and angiotensin converting inhibitors, particularly lisinopril, enalapril, captopril, and benazepril. A particularly preferred group of drugs is lisinopril, acyclovir, metformin hydrochloride, baclofen, ciprofloxacin, furosemide, cyclosporin, sertraline hydrochloride, and calcium carbonate. The drug that is contained in the immediate-release portion of the tablet is a sparingly soluble or insoluble drug, such as those listed above. Combinations of particular interest are metformin hydrochloride in the controlled-released portion and a sulfonylurea such as glimerpiride, glyburide, or glipizide in the immediate-release portion. Metformin hydrochloride and glimepiride are particularly preferred.

The following examples are offered for purposes of illustration only and are not intended to limit the scope of the invention.

EXAMPLES

Tablets containing 500 mg of metformin hydrochloride and 2.10 mg of glimepiride were made by the following procedure.

Preformed Metformin hydrochloride tablets were used that included 500 mg of metformin hydrochloride and a matrix containing approximately equal proportions by weight of hydroxypropyl methylcellulose and poly(ethylene oxide) to form a 1000 mg tablet. A solution was then prepared by dissolving four parts of Polysorbate 80 (polyethylene sorbitan monooleate) in 715 parts of deionized water, all by weight. Glimepiride in particulate form (1.60 parts by weight, 2–4 micron diameter particle size) was then dispersed in the Polysorbate 80 solution, and Opadry YS-1-19025-A Clear (hydroxypropyl methyl cellulose, available from Colorcon, West Point, Pa., USA) was added in an amount of 80 parts by weight. The resulting suspension was sprayed onto the metformin hydrochloride tablets at a rate of 5 g/min until the tablet weight increased by 11.2%.

The foregoing is offered primarily for purposes of illustration. It will be readily apparent to those skilled in the art that further drugs can be included, and that the shapes, components, additives, proportions, methods of formulation, and other parameters described herein can be modified further or substituted in various ways without departing from the spirit and scope of the invention.

What is claimed is:

1. A method for the manufacture of a pharmaceutical tablet which upon oral ingestion delivers a first drug by substantially immediate release and a second drug by sustained release defined as a release rate into gastric fluid that is slow enough to leave at least about 40% of said second drug unreleased one hour after ingestion, and in which said first drug is at most sparingly soluble in water and the weight ratio of said first drug to said second drug is equal to or less than about 0.01:1, said method comprising:

dispersing said second drug in a solid matrix to form a unitary core which upon immersion in gastric fluid releases said second drug by sustained release while retaining at least a portion of the mass of said solid matrix as a coherent body until said second drug is fully released therefrom;

depositing on the surface of said unitary core an aqueous suspension of particles of said first drug that are equal to or less than about 10 microns in diameter, using an amount of said first drug selected to achieve said weight ratio relative to said second drug; and evaporating water from said aqueous suspension thus deposited to leave a solid shell encasing said unitary core and containing said first drug.

2. A method for the manufacture of a pharmaceutical tablet which upon oral ingestion delivers a first drug by substantially immediate release and a second drug by sustained release defined as a release rate into gastric fluid that is slow enough to leave at least about 40% of said second drug unreleased one hour after ingestion, and in which said first drug is at most sparingly soluble in water and the weight ratio of said first drug to said second drug is equal to or less than about 0.01:1, said method comprising:

combining said second drug with a first solid matrix to form a sustained-release layer, said first solid matrix being of a substance which when formed into a coherent body and immersed in gastric fluid releases said second drug by sustained release while retaining at least a portion of the mass of said first solid matrix as a coherent body until said second drug is fully released therefrom; and combining particles of said first drug that are equal to or less than about 10 microns in diameter with particles of a second solid matrix to form an immediate-release layer adjoined to said sustained-release layer as a layered tablet, said second solid matrix being of a substance that separates into discrete matrix particles immediately upon immersion in gastric fluid, using amounts of said first and second drugs selected to achieve said weight ratio.

3. A method in accordance with claims 1 or 2 in which said weight ratio is from about 0.001:1 to about 0.01:1.

4. A method in accordance with claims 1 or 2 in which said particles of said first drug are from about 0.3 micron to about 10 microns in diameter.

5. A method in accordance with claims 1 or 2 which said particles of said first drug are from about 1 micron to about 5 microns in diameter.

6. A method in accordance with claims 1 or 2 in which said first drug has a solubility in water at 37° C. of less than 2% by weight.

7. A method in accordance with claims 1 or 2 in which said first drug has a solubility in water at 37° C. of less than 0.5% by weight.

8. A method in accordance with claims 1 or 2 in which said first drug is a sulfonylurea and said second drug is a member selected from the group consisting of metformin hydrochloride, vancomycin hydrochloride, captopril, erythromycin lactobionate, ranitidine hydrochloride, sertraline hydrochloride, ticlopidine hydrochloride, amoxicillin, cefuroxime axetil, cefaclor, clindamycin, doxifluridine, tramadol, fluoxitine hydrochloride, ciprofloxacin, gancyclovir, bupropion, lisinopril, cefaclor, ciprofloxacin, saguinavir, ritonavir, nelfinavir, clarithromycin, azithromycin, ceftazidine, cyclosporin, digoxin, paclitaxel, iron salts, topiramate, and ketoconazole.

9. A method in accordance with claims 1 or 2 in which said first drug is a sulfonylurea selected from the group consisting of glimepiride, glyburide, and glipizide, and said second drug is metformin hydrochloride.

10. A method in accordance with claims 1 or 2 in which said first drug is glimepiride and said second drug is metformin hydrochloride.

11. A method in accordance with claims 1 or 2 in which said solid matrix is a member selected from the group consisting of poly(ethylene oxide), hydroxypropyl methyl cellulose, and combinations of poly(ethylene oxide) and hydroxypropyl methyl cellulose.

12. A method in accordance with claim 1 in which said aqueous suspension has a suspending agent dissolved therein.

13. A method in accordance with claim 12 in which said suspending agent is hydroxypropyl methyl cellulose.

14. A method in accordance with claim 2 in which said second solid matrix is a member selected from the group consisting of lactose, microcrystalline cellulose, and combinations of lactose and microcrystalline cellulose.

* * * * *